United States Patent [19]

Kaneko

[11] Patent Number: 4,982,326
[45] Date of Patent: Jan. 1, 1991

[54] METHOD FOR ANALYZING AUTORADIOGRAPH FOR DETERMINING BASE SEQUENCE OF NUCLEIC ACID

[75] Inventor: Takashi Kaneko, Hadano, Japan

[73] Assignee: Fuji Photo Film Co., Ltd., Minami-ashigara, Japan

[21] Appl. No.: 420,603

[22] Filed: Oct. 4, 1989

Related U.S. Application Data

[63] Continuation of Ser. No. 22,632, Mar. 5, 1987, abandoned.

[30] Foreign Application Priority Data

| Mar. 5, 1986 | [JP] | Japan | 61-47924 |
| Mar. 12, 1986 | [JP] | Japan | 61-55481 |
| Mar. 12, 1986 | [JP] | Japan | 61-55482 |
| Mar. 12, 1986 | [JP] | Japan | 61-55483 |

[51] Int. Cl.$^5$ .......... G06F 15/42; C12Q 1/68; G01N 33/50; G01N 30/00
[52] U.S. Cl. .......... 364/413.01; 435/6; 935/86; 935/87
[58] Field of Search .......... 364/413.01; 935/77, 935/78, 86, 87; 435/6, 808

[56] References Cited

FOREIGN PATENT DOCUMENTS

0062298 9/1986 Japan.
0062299 9/1986 Japan.

OTHER PUBLICATIONS

European search report for EP 240729, search report published Aug. 24, 1988.
Smith, L. M. "Fluorescence Detection in Automated DNA Sequence analysis" *NATURE*, vol. 321, Jun. 12, 1986, 674–678.

*Primary Examiner*—Clark A. Jablon
*Attorney, Agent, or Firm*—Sixbey, Friedman, Leedom & Ferguson

[57] ABSTRACT

A method of analyzing an autoradiograph of plural resolved rows which are formed by resolving base-specific DNA fragments or base-specific RNA fragments labeled with a radioactive element in one-dimensional direction on a support medium, to determine the base sequence of nucleic acids by:
(1) electrically displaying the autoradiograph as an image on a screen on the basis of digital signals corresponding to said autoradiograph;
(2) displaying a read cursor on the screen; and
(3) displaying a name of a base to which a band is assigned on the screen, which is determined by using the read cursor, together with the read cursor. A method of analyzing an autoradiograph which comprises recording and storing pattern information, cursor information and base sequence information, and a method which comprises verifying and/or correcting the determined sequence of bands are also disclosed.

35 Claims, 6 Drawing Sheets

FIG. 11

GAGATTCCCATGCAGG·············

FIG. 12

| | | | |
|---|---|---|---|
| 1 | $x_1$ | $y_1$ | T |
| 2 | $x_2$ | $y_2$ | G |
| 3 | $x_3$ | $y_3$ | C |
| 4 | $x_4$ | $y_4$ | A |
| 5 | $x_5$ | $y_5$ | T |
| 6 | $x_6$ | $y_6$ | C |
| ⋮ | ⋮ | ⋮ | ⋮ |

METHOD FOR ANALYZING AUTORADIOGRAPH FOR DETERMINING BASE SEQUENCE OF NUCLEIC ACID

This application is a continuation of Ser. No. 07/022,632, filed Mar. 5, 1987, now abandoned.

BACKGROUND OF THE INVENTION

1. Field of the Invention

The present invention relates to a method of analyzing autoradiograph for determining the base sequence of nucleic acids.

2. Description of the Prior Art

It is essential to obtain genetic information carried by organisms in order to make the function or replication mechanism of the organism clear in the field of molecular biology and biotechnology which have been rapidly developed in recent years. Particularly, it is essential to determine the base sequence of nucleic acids such as DNA (or DNA fragment; the same applies hereinbelow) which carries specific genetic information.

Maxam-Gilbert method and Sanger-Coulson method are known as typical methods for determining the base sequence of nucleic acids such as DNA and RNA. In the former Maxam-Gilbert method, a group containing a radioactive isotope such as $^{32}P$ is attached to a chain molecule of DNA at one end to label it with the radioactive element and the bond between the constitutional units of the chain molecule is base-specifically cleaved by a chemical reaction. A mixture of the resulting base-specific DNA cleavage products is resolved (developed) through gel electrophoresis to obtain a resolved pattern (not visible) wherein each of the numerous cleavage products is resolved on the gel support medium. The resolved pattern is visualized on a radiographic film such as an X-ray film to obtain an autoradiograph thereof as a visible image. The bases in the certain positional relationships with the end of the radioactive element-attached chain molecule can be sequentially determined according to the visualized autoradiograph and the applied base-specific cleavage means. In this way, the sequence for all bases of the DNA specimen can be determined.

In the latter Sanger-Coulson method, synthetic DNA products which are complementary to the chain molecule of DNA and radioactively labeled, are base-specifically synthesized by utilizing a chemical reaction, and the obtained mixture of numerous synthetic DNA products is resolved on a support medium by gel electrophoresis to obtain a resolved pattern. In a similar manner to that described above, the base sequence of DNA can be determined according to the visualized autoradiograph.

The base sequence of the nucleic acids has been conventionally determined by visually judging individual resolved positions (bands) of the base-specific cleavage products or the base-specific synthetic products of radioactively labeled nucleic acid (hereinafter referred to simply as base-specific fragments of nucleic acid) on the visualized autoradiograph and comparing the positions of the bands among them. Namely, the analysis of the autoradiograph is done by observing the visualized autoradiograph with eyes, and such visual analysis requires great amounts of time and labor. Further, since the visual analysis of the autoradiograph varies or fluctuates owing to the skill of investigators, the results on the determination of the base sequence of nucleic acid vary depending on the investigators and the accuracy of information is limited to a certain extent.

For instance, the analysis of the autoradiograph is made in such a manner that an X-ray film having the visualized autoradiograph is fixed onto a sharcastene and then a cursor made of a plastic (a measure plate for reading) placed on the sharcastene is manually moved on the film up and down (or right and left) to visually judge the relative positions of the radioactively labeled substances (bands) using the cursor as a measure. On the center of the transparent plastic cursor (so-called hair line cursor), a fine straight line is usually drawn. The hair line cursor can be moved in one direction (in the direction parallel to the film), while fixed to the sharcastene. When the radioactively labeled substances are ideally resolved, that is, when resolved rows are approximately straight and the radioactively labeled substances of each row are resolved at the same velocity, the relative positions of bands among the resolved rows can be easily determined by using the straight cursor to thereby sequence the bands.

However, the resolved pattern often causes a smiling phenomenon or offset distortion. The smiling phenomenon is a phenomenon in which migration distances of the radioactively labeled substances at the both sides of the support medium are shorter than that in the vicinity of the center thereof. This phenomenon is caused by heat dissipation effect (so-called edge effect), etc. during the resolving procedure such as electrophoresis. The offset distortion is a phenomenon in which the positions of resolved rows (lanes) are wholly deviated from one another and is caused by difference between the slots in the resolution-starting positions or time of samples, which is due to the unevenness of the shapes of slots, etc. Besides the deviation of the bands from one another, there is a possility that the disorder of the bands themselves and the zigzag of the lanes are caused.

In such a case, the positional relationship between the bands cannot be judged by using the hair line cursor alone, because the cursor is straight, fixed to the device and allowed only to make a parallel movement. Analyzers have paid close attention to the determination of the sequence of bands and corrected the deviation of positions and the disorder with eyes so as not to misread the sequence of bands. Accordingly, the hair line cursor is only a rough measure for reading.

Alternatively, an analyzing method utilizing a computer system using a digitizer board, etc. has been attempted, in which the X-ray film having the visualized autoradiograph is fixed onto the digitizer board which has two-dimensional coordinates and is online to the computer system and then names of bases to which bands are assigned are inputted through other inputting means such as a keyboard while indicating the bands on the film with an indicating stick. According to this method, sequence and base name are automatically given to each band based on the coordinates inputted by the indicating stick.

There is another problem that the read bands and unread bands are hardly distinguished from each other in the above-mentioned methods using the sharcastene and the computer system. These methods have further disadvantages in that eyes in reading the bands on the X-ray film differs from eyes upon the keyboard to input base name and that there is a time interval therebetween. Thus, the reversal of the sequence of bands, misreading such as overlapping or overlooking of bands, or the mis-inputting of base names cannot be prevented.

The obtained base sequence of nucleic acids has been recorded and stored in a recording material such as a paper or in a recording medium such as a magnetic disk. Since the information on the base sequence determined on the basis of the autoradiograph are stored in a medium different from that on which the information on the autoradiograph of the resolved pattern is recorded, namely the X-ray film, it is difficult that both are allowed to collate to each other.

More in detail, the relationship between the resolved pattern and base sequence information included in the pattern is clear during the analysis of the autoradiograph. However, after the analysis is completed and base sequence information is recorded on other medium, it is very difficult to make one of them correspond to the other again. Hence, there are further problems that the analysis must be done all over again when the analysis is interrupted, or it requires much time and labor same as in the analysis when the analytical results are verified. Pattern information and base sequence information are respectively valuable as a series of information, both infomation being recorded and stored in the different mediums in the different forms. However, it is impossible that the both mediums are allowed to correspond one-to-one to each other immediately.

There have been disclosed by the present applicant (or the assignee) in U.S. patent application Nos. 664,405, abandoned and continued in U.S. Ser. Nos. 07/423,686 and 837,037, abandoned and continued in U.S. Ser. No. 07/378,509, autoradiographic procedures which utilize a radiation image recording and reproducing method using a stimulable phosphor sheet for obtaining the autoradiograph of radioactively labeled substances resolved on a support medium, in place of the conventional radiography using a radiosensitive film. Said stimulable phosphor sheet comprises a stimulable phosphor and has such properties that when exposed to a radiation, the stimulable phosphor absorbs a portion or radiation energy and then emits light (stimulated emission) corresponding to the radiation energy stored therein upon excitation with an electromagnetic wave (stimulating rays) such as visible light or infrared rays. According to this method, exposure time can be greatly shortened and there is no fear of causing problems such as chemical fog associated with prior arts. Further, since the autoradiograph having information on radioactively labeled substances is stored in the phosphor sheet as radiation energy and then read out photoelectrically as stimulated emission, the autoradiograph can be directly obtained as digital signals and then recorded on a suitable recording medium to store it.

There are also proposed in U.S. patent application Nos. 568,875, now U.S. Pat. No. 4,868,746, No. 568,877, now abandoned, and continued as U.S. patent application No. 07/024,909, now U.S. Pat. No. 4,777,597, No. 849,187, abandoned and continued as U.S. patent application No. 07/541,197 and No. 854,381, now U.S. Pat. No. 4,720,786, methods for automatically determining the base sequence of nucleic acids by obtaining the autoradiograph as digital signals and subjecting the digital signals to appropriate signal processing.

SUMMARY OF THE INVENTION

It is an object of the present invention to provide a method of analyzing autoradiograph, which allows the determination of the base sequence of nucleic acids to be done with high accuracy.

It is another object of the present invention to provide a method of analyzing autoradiograph, which allows the determined base sequence to be easily verified.

The present invention provides in the first aspect a method of analyzing an autoradiograph of plural resolved rows which are formed by resolving base-specific DNA fragments or base-specific RNA fragments labeled with a radioactive element in one-dimensional direction on a support medium, to determine the base sequence of nucleic acids, which comprises steps of:

(1) electrically displaying the autoradiograph as an image on a screen on the basis of digital signals corresponding to said autoradiograph;

(2) displaying a read cursor on the screen; and (3) displaying a name of a base to which a band is assigned on the screen, which is determined by using the read cursor, together with said read cursor.

It is other object of the present invention to provide a method of analyzing autoradiograph, which allows the information on the resolved pattern and the information on the base sequence of nucleic acids to be stored while keeping the one-to-one correspondence.

It is another object of the present invention to provide a method of analyzing autoradiograph, which allows the analysis for the determination of the base sequence to be interrupted or recommenced at any time.

It is another object of the present invention to provide a method of analyzing autoradiograph, which allows the determined base sequence to be easily verified.

The present invention provides in the second aspect a method of analyzing an autoradiograph of a resolved pattern comprising plural resolved rows which are formed by resolving base-specific DNA fragments or base-specific RNA fragments labeled with a radioactive element in one-dimensional direction on a support medium, to determine the base sequence of nucleic acids, which comprises separating information on said autoradiograph and the base sequence of nucleic acid determined on the basis of the autoradiograph into the following three kinds of information:

(1) information on the autoradiograph of the resolved pattern;

(2) information on plural read cursors which pass through bands on the autoradiograph and indicate relative positions of the bands; and (3) information on the sequence of bases to which the bands on the autoradiograph are assigned;

and recording and storing said information in such a manner as to establish a correspondence between the pattern information (1) and the cursor information (2) and a correspondence between the cursor information (2) and the base sequence information (3).

It is another object of the present invention to provide a method of analyzing autoradiograph, which allows the verification and/or the correction of the determined sequence of bands to be made easily and advantageously.

The present invention provides in the third aspect a method of analyzing an autoradiograph of a resolved pattern comprising plural resolved rows which are formed by resolving base-specific DNA fragments or base-specific RNA fragments labeled with a radioactive element in one-dimensional direction on a support medium, to determine the base sequence of nucleic acids, which comprises steps of:

(1) electrically displaying an autoradiograph in which sequence of bands has been determined as an image on a screen on the basis of digital signals corresponding to said autoradiograph;

(2) displaying a read cursor on the screen to fix the cursor to the autoradiograph so as to allow the cursor to traverse the resolved rows and to pass through one band position according to input for verification of the band's sequence, and displaying the base name of said band together on the screen;

(3) displaying a read cursor on the screen to fix the cursor to the autoradiograph so as to allow the cursor to pass through a band position adjacent to the band to which the cursor is fixed in the second step according to input for verification of the band's sequence, and displaying the base name of said band together on the screen; and (4) repeating the third step to verify the determined sequence of the bands on the autoradiograph.

The present invention provides in the fourth aspect a method of analyzing an autoradiograph of a resolved pattern comprising plural resolved rows which are formed by resolving base-specific DNA fragments or base-specific RNA fragments labeled with a radioactive element in one-dimensional direction on a support medium, to determine the base sequence of nucleic acids, which comprises steps of:

(1) electrically displaying an autoradiograph in which sequence of bands has been determined as an image on a screen on the basis of digital signals corresponding to said autoradiograph;

(2) displaying a read cursor on the screen to fix the cursor to the autoradiograph so as to allow the cursor to traverse the resolved rows and to pass through one band position according to input for verification of the band's sequence, and displaying the base name of said band together on the screen;

(3) displaying a read cursor on the screen to fix the cursor to the autoradiograph so as to allow the cursor to pass through a band position adjacent to the band to which the cursor is fixed in the second step according to input for verification of the band's sequence, and displaying the base name of said band together on the screen;

(4) deleting, adding or changing the read cursor and/or the base name displayed in the third step according to input, when there is inputted information on the basis of the display screen; and (5) repeating in order the third and fourth steps to thereby verify and correct the determined sequence of the bands.

The term "the determination of the band's sequence" or "the determination of the sequence of bands" used herein means that sequence is given to bands on the basis of the position of each band along the resolved direction and base names are given to the bands on the basis of the resolved rows to which the bands belong.

BRIEF DESCRIPTION OF THE DRAWINGS

FIG. 11 is a diagram showing an example of a series of base names stored as base sequence information.

FIG. 12 is a diagram showing an example of band information on the determined sequence of bands.

DETAILED DESCRIPTION OF THE INVENTION

Figure 1:
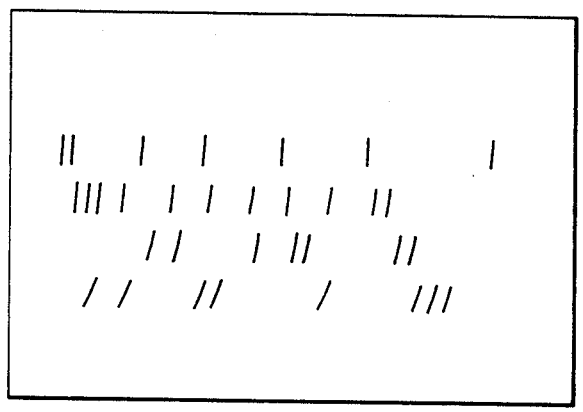
FIG. 1 is a diagram showing an example of an autoradiograph of an electrophoretic pattern displayed as a shading image on a screen.

According to the first method of the present invention, a read cursor is displayed on a screen having a visualized autoradiograph and can be moved arbitrarily thereon without being fixed to a device such as sharcastene. Further, the read cursor and the base name of a band determined and inputted on the basis of said read cursor are together displayed on the screen, unlike the method using the sharcastene or the digitizer board. Since it is clear to which band there has been read, it can be prevented to read bands reversely, to overlook bands or to read bands repeatedly. Since the base names of bands inputted are immediately displayed on the same screen, the read operation can be proceeded confirming and verifying the corresponding relationship between the read bands, the cursor and the base names. There can be eliminated mis-display (missing in input) of base names or errors in the input of base names due to time and spatial intervals.

Therefore, the base sequence of nucleic acids can be determined in a short time with high accuracy.

The error during the read and input procedures can be more prevented by distinguishing the cursor used for reading from the unused cursor by means of color, design or brightness, and further by distinguishing a box of the inputted and displayed base name from a box of the undisplayed base name in a similar manner.

Further, the read cursor can be arbitrarily prepared on the screen, unlike the conventional method using the sharcastene. Even when the positions of bands among the lanes of the resolved pattern are deviated from one another by the smiling phenomenon or the offset distortion, a cursor in any form such as a broken line, a curved line, etc. can be prepared along the bands and the optimum cursor can be individually prepared for every pattern to display it on the screen. The cursor can be automatically prepared in a short period of time according to input of positions along the bands of each lane. This means that the cursor can be easily re-prepared when the prepared cursor is insufficient or no longer agrees with the bands on the way of reading.

The cursor displayed on the screen can be moved not only in parallel (up and down or right and left), but also in an arbitrary direction. Namely, even when the resolved pattern is curved in zigzag, the cursor can be moved optimumly.

Accordingly, while moving the prepared read cursor along the resolved direction, analyzers can directly read the relative positions of bands on the basis of the cursor and the read bands are as such sequenced. It is not necessary to correct the deviated band positions with eyes by using the straight cursor as a measure or to make a supplement to wrong bands by the analyzer, unlike the conventional method. Further, it is not necessary to read the band positions, while memorizing the positional relationship of the bands before and behind. This also brings about the prevention of the reversal of the band's sequence, the overlapping and the overlooking of the bands in reading, and there can be determined the base sequence of nucleic acids with high accuracy by surely reading the positions of the bands. Further, since the sequence can be directly given to the bands on the basis of the read cursor, the bands are accurately read as compared with the case where the sharcastene and hair line cursor are used. In addition thereto, the base sequence of nucleic acids can be determined by simply giving the sequence to the bands in a short time without paying close attention or requiring great skill as in the conventional methods.

According to the second method of the present invention, information on the read cursor corresponding to each band on the autoradiograph is recorded and stored in addition to information on the autoradiograph of the resolved pattern and information on the base sequence of nucleic acid determined on the basis of said autoradiograph, and said base sequence information is stored as the base names corresponding to the cursors (that is, bands), so that information on the autoradiograph and information on the base sequence can be recorded and stored being kept in the one-to-one correspondence.

Thus, the autoradiograph of the resolved pattern and the base sequence of nucleic acid can be displayed in the clear one-to-one correspondence by means of the read cursors each of which passes through one band on the autoradiograph and the base name to which the band is assigned. Since the pattern information, the read cursor information and the base sequence information are separately recorded and stored in a suitable recording medium, they can be displayed on an arbitrary recording material or a display screen such as CRT at any time, while the one-to-one correspondence therebetween is kept.

When the base sequence of nucleic acid on the analyzed autoradiograph is to be verified by other people, the verification can be easily made at any time. When the interrupted analysis of the autoradiograph is to be recommenced, the analysis can be recommenced from part of the way. It is clearly found in the verification of the base sequence whether the assignment of the band is correct or not. The analysis is allowed to be made from part of the way without requiring the reading from the beginning.

There can be extracted one or more of said pattern information, cursor information and base sequence information which are separately recorded and stored. Thus, the application of base sequence information to another resolved pattern of the same nucleic acid or the application of only cursor information to a different resolved pattern becomes possible.

Accordingly, the determination of the base sequence of nucleic acids is allowed to proceed advantageously without any limitation to the analysis of the autoradiograph.

According to the third and fourth methods of the present invention, the base sequence is displayed together with the autoradiograph and the base sequence is not given as a character string all together but given one base by one base in a one-to-one correspondence to the bands, when the base sequence of nucleic acid which has been determined by sequencing the bands on the autoradiograph is verified, so that the base sequence can be surely verified one band by one band. The base name and the band are allowed to correspond téte-á-téte to each other by a read cursor of straight line or broken line, so that an error in the sequence of the bands and the overlapping or overlooking of the band in reading can be found immediately.

Further, when an error in the sequence (order and base name) of the band and the overlapping or overlooking of the band in reading are detected in the course of the verification, the correction can be simply made in situ. In the correction, display is also made in order one band by one base so that the correction can be made without causing any error.

Accordingly, the reliability of the base sequence finally obtained can be remarkably enhanced.

Particularly, when the first determination of the sequence of bands is automatically made through the signal processing as afore-described, investigators wish to make further correction. In such a case, the method of the present invention is very effective.

Examples of samples employable in the present invention include mixtures of base-specific fragments of nucleic acids such as DNA and RNA labeled with a radioactive element. The term "fragments" of nucleic acids mean portions of a long-chain molecule. For instance, a mixture of base-specific DNA cleavage products, which is a kind of a mixture of base-specific DNA fragments, can be obtained by base-specifically cleaving the radioactively labeled DNA according to the aforementioned Maxam-Gilbert method. A mixture of base-specific DNA synthetic products can be obtained by synthesizing from radioactively labeled deoxynucleoside triphosphate and DNA polymerase by use of DNA as a template according to the aforementioned Sanger-Coulson method.

Mixtures of base-specific RNA fragments can be also obtained as a mixture of cleavage products of a mixture of synthetic products in the similar manner to the DNA methods. DNA is composed of four kinds of bases: adenine, guanine, thymine and cytosine as its constitutional units, and RNA is composed of four kinds of bases: adenine, guanine, uracil and cytosine. These substances can be labeled with a radioactive element such as $^{32}P$, $^{14}C$, $^{35}S$, $^{3}H$ or $^{125}I$ by any of appropriate methods.

A sample, which is a mixture of the base-specific fragments of a nucleic acid labeled with a radioactive element, can be resolved (developed) on a known support medium such as a gel support medium by any of conventional resolving (developing) procedures such as electrophoresis, thin layer chromatography, column chromatography and paper chromatography.

Now, the method of analyzing autoradiograph of the present invention will be described by referring to determination of base sequence of DNA.

In the first method of the invention, an electrophoretic pattern formed on a support medium with a combination of the following four groups of base-specific DNA fragments labeled with a radioactive element is autoradiographed by means of the conventional radiography using a radiosensitive material or the radiation image recording and reproducing method using a stimulable phosphor sheet. The digital signals corresponding to the autoradiograph are then obtained through an appropriate read-out system.

(1) guanine (G)—specific DNA fragments,
(2) adenine (A)—specific DNA fragments,
(3) thymine (T)—specific DNA fragments,
(4) cytosine (C)—specific DNA fragments.

Each group of the base-specific DNA fragments is composed of base-specific cleavage products or synthetic products which have various lengths and the same base at terminals.

When the conventional radiography is used, the support medium and a radiosensitive material such as an X-ray film are placed together in layers at a low temperature or room temperature for a long period of time (several to several tens of hours) to expose the radiographic film. The radiographic film is then developed to visualize the autoradiograph of the radioactively labeled substances on the film, and the visualized autoradiograph is read out by using an image read-out system. For instance, the radiographic film is irradiated with an optical beam and the beam transmitted thereby or reflected therefrom is photoelectrically detected, whereby the visualized autoradiograph can be transformed to electric signals. Further, the electric signals are converted into digital signals corresponding to the autoradiograph through A/D conversion.

When the radiation image recording and reproducing method is used, the support medium and the stimulable phosphor sheet are placed together in layers at an ambient temperature for a short period of time (several seconds to several tens of minutes) to store radiation energy radiated from the radioactively labeled substances in the phosphor sheet, whereby the autoradiograph is recorded as a kind of a latent image (energy-stored image) on the phosphor sheet. The stimulable phosphor sheet, for instance, has a basic structure where a support comprising a plastic film, a phosphor layer comprising a stimulable phosphor such as a divalent europium activated barium fluorobromide phosphor ($BaFBr:Eu^{2+}$) and a transparent protective film are laminated in this order. The stimulable phosphor has characteristics of absorbing and storing radiation energy when irradiated with a radiation such as X-rays and subsequently releasing the stored radiation energy as stimulated emission when excited with visible light or infrared rays.

Then, the autoradiograph stored and recorded on the stimulable phosphor sheet is read out by using a read-out system. For instance, the phosphor sheet is scanned with a laser beam to release the radiation energy stored in the stimulable phosphor as light emission and the emitted light is photoelectrically detected, so that the autoradiograph can be directly obtained as electric signals without the visualization thereof. Further, the electric signals are converted into digital signals corresponding to the autoradiograph through A/D conversion.

The above-described methods for measuring the autoradiograph and obtaining the digital signals corresponding thereto are described in more detail in the aforementioned U.S. patent applications Ser. No. 568,875, now U.S. Pat. No. 4,868,746, Ser. No. 568,877, now U.S. Pat. No. 4,777,597, and Ser. No. 837,037, abandoned and continued as Ser. No. 07/378,509.

While the methods for obtaining the digital signals corresponding to the autoradiograph using the conventional radiography and the radiation image recording and reproducing method are described above, the present invention is not limited thereto and digital signals obtained by any other methods can be applied to the analyzing method of the present invention, provided that they correspond to the autoradiograph.

In the above read-out procedure, it is not always necessary to conduct the read-out operation of the autoradiograph all over the surface of the radiographic film or the stimulable phosphor sheet. Only the image region may be subjected to the read-out operation.

Otherwise, there may be previously inputted information on the location of each resolved row and the width of band to preset read-out conditions and then conducted scanning at a scanning line density such that each band is traversed by at least one scanning lines in the read-out operation, so as to shorten read-out time and obtain efficiently necessary information. The digital signals corresponding to the autoradiograph in the invention also include the thus-obtained digital signals.

The obtained digital signals $D_{xy}$ comprise a coordinate (x,y) which is represented by a coordinate system fixed to the radiographic film or the stimulable phosphor sheet and a signal level (z) at the coordinate. The signal level represents the density of image at the coordinate, that is, the amount of the radioactively labeled substances. Accordingly, a series of the digital signals (namely, digital image data) have information on two-dimensional location of the labeled substances.

The digital signals corresponding to the autoradiograph are stored temporarily in a memory device (that is, stored in a non-volatile memory unit such as a buffer memory, a magnetic disk, etc.) and then transferred to a apparatus comprising a signal processing circuit; a display means (e.g., CRT) capable of displaying together an autoradiograph, a cursor and a base name column; an input means capable of conducting input for the movement of the cursor, the display of base name and further the preparation of the cursor; and a storage means capable of storing pattern information, cursor information and base sequence information, to visualize the autoradiograph (the resolved pattern of the radioactively labeled substances) as an image on the display screen thereof.

The digital signals may be previously subjected to signal processing (image processing) to give a well readable image having well adjusted density and contrast. Examples of the image processing include spatial frequency processing, gradation processing, addition average processing, reduction processing and enlarging processing.

The autoradiograph to be displayed on the screen may be an image having various shade in density (shading image) wherein signal level (image density which is proportional to the amount of the radioactively labeled substances) at the coordinate set on the screen is represented by color lightness, being similar to a conventional radiographic image (namely, a black and white image). The autoradiograph may be a binary image represented in a simplified form by converting signal levels into a binary system.

Alternatively, the autoradiograph may be an image (namely, a bird's-eye view) represented by multi-displaying two-dimensional waveforms composed of one-dimensional positions (positions along electrophoretic direction) and signal levels at regular intervals in a direction perpendicular to the electrophoretic direction. According to the bird's-eye view, the amount of the radioactively labeled, substances is represented three-dimensionally as the height in the bird's-eye view, so that the peak positions of the bands can be accurately read, the positional relationship of the bands between the electrophoretic rows (lanes) can be easily understood and the separation of the bands can be easily made in the region where band's spaces are dense in the vicinity to the electrophoresis-starting position. The method of displaying the autoradiograph by the bird's-eye view is described in more detail in our co-pending U.S. patent application Ser. No. 898,000, now abandoned and continued as Ser. No. 07/373,613.

FIG. 1 shows an example of the autoradiograph of the electrophoretic pattern displayed as a shading image on a screen.

Figure 2:
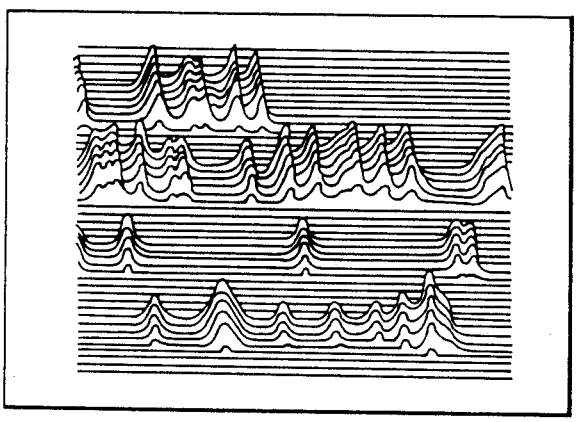
FIG. 2 is a diagram showing an example of an autoradiograph of an electrophoretic pattern displayed as a bird's-eye view on a screen.
Figure 3:
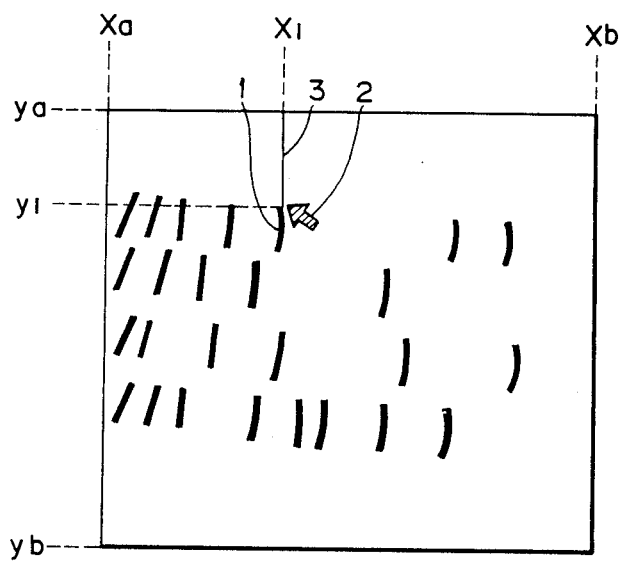
FIGS. 3 to 6 are each a diagram showing an example of an autoradiograph displayed on a screen and illustrates the preparation of a read cursor.
Figure 4:
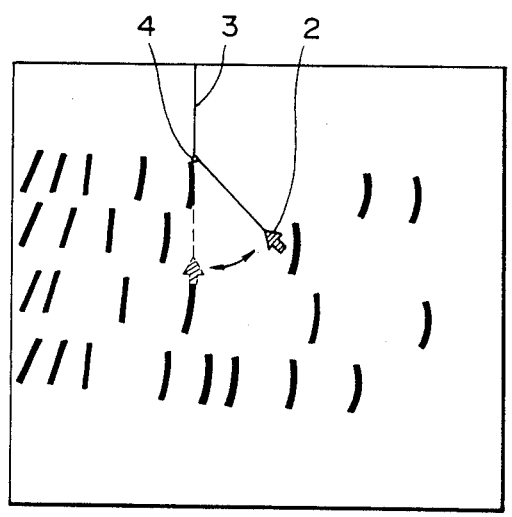

FIG. 2 shows another example of the autoradiograph of the electrophoretic pattern displayed as a bird's-eye view on a screen.

In the second place, the read cursor is displayed on the screen.

The read cursor may be displayed in the form of a simple straight line traversing the lanes. The read cursor is preferably displayed in the form of a broken line or a curved line along a band of each lane, when the band positions on the electrophoretic pattern are deviated from one another or the bands are dislocated by the smiling phenomenon, the offset distortion, etc.

The read cursor is prepared for instance, in the following procedure to be displayed on the screen.

FIGS. 3 to 6 show examples of the autoradiograph of the electrophoretic pattern displayed as a shading image on a screen and illustrate the preparation of a read cursor. In FIGS. 3 to 6, the electrophoretic direction is the right and the smiling phenomenon occurs on the electrophoretic pattern.

A perpendicular line is drawn from the top on the screen (top of the display region of the autoradiograph) to an inputted position which is decided on the basis of the display screen. The first position to be inputted is preferably a position of a band on a lane at the upper end of the pattern (see, numeral 1 in FIG. 3), because the read cursor is prepared from said position as the starting point.

The input of information on the position is conducted by means of a mouse cursor, a light pen or a joystick. From the viewpoint of accuracy in position, the mouse cursor is preferred. The input with the mouse cursor is done by use of a mouse cursor which is displayed in the form of an arrow (→) on the screen and capable of arbitrarily moving thereon (see, numeral 2 in FIG. 3) and an input means which can move the mouse cursor arbitrarily and by which information on the position of the mouse cursor is inputted (not shown in FIG. 3).

For instance, a square region where the autoradiograph is displayed on the screen is represented by the coordinates $(x_a, y_a)$ and $(x_b, y_b)$ and the position of the mouse cursor is represented by the coordinate $(x_m, y_m)$. When a position where $x_m = x_1$, $y_m = y_1$ is inputted by means of the mouse cursor, a segment $(x_1, y_a)(x_1, y_1)$ is displayed on the screen (see, numeral 3 in FIG. 3).

Figure 5:
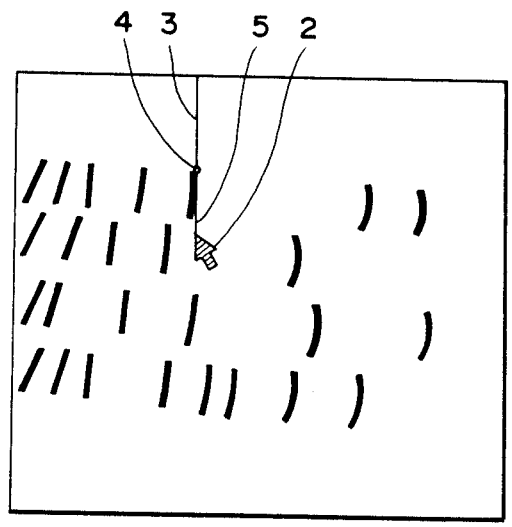

Subsequently, a straight line is drawn from the position of the starting point to another inputted position (the second position) on the inside of the starting point in the electrophoretic pattern. The input of the position is made in a similar manner to that described above. First, a segment $(x_1, y_1)(x_m, y_m)$ between the starting point 4 $(x_1, y_1)$ and the position $(x_m, y_m)$ of the mouse cursor 2 is displayed. When the mouse cursor 2 is moved, said segment disappears on the screen and a new segment between the starting point 4 and the moved position appears. The mouse cursor can be freely moved within the square region represented by the coordinates $(x_a, y_a)$ and $(x_b, y_b)$. Such a segment joining the starting point 4 to each of the moved positions of the mouse cursor 2 is displayed every time with the movement of the mouse cursor. When the input of position is made at a position where the segment suitably traverses the lanes, a next segment 5 jointed to the segment 3 is fixed to the screen, as shown in FIG. 5.

In this way, segments $(x_i, y_i)(x_{i+1}, y_{i+1})$ (wherein i is a positive integer) are drawn in order so as to allow the segments to traverse the lanes from the upper lane to the lower lane along bands of each lane. The sample is an exclusive combination of the above-described four groups of the base-specific DNA fragments and there is no possibility that the band of each lane exists at the same position (at the same electrophoretic distance). The term "along the bands" means that a segment is drawn along the bands in a broad sense so as to allow the electrophoretic distances of the lanes to be equal to one another, and does not mean that each segment is exactly passed on the band of each lane.

Figure 6:
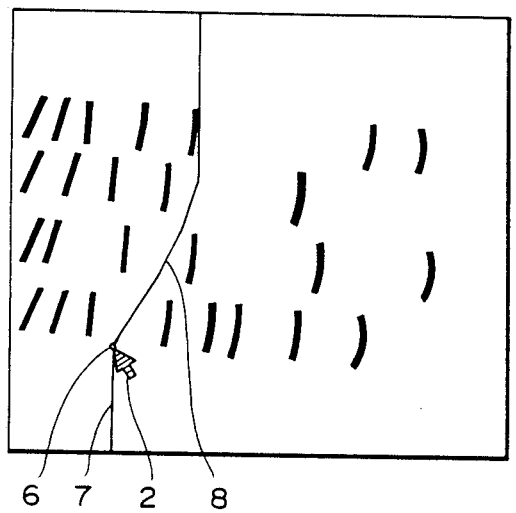

When segments completely traverse the electrophoretic pattern, a perpendicular segment 7 $(x_i, y_i)(x_b, y_b)$ is drawn from a finally inputed position 6 to the lower end of the square region according to input of that the position finally inputted is an end point inputted, as shown in FIG. 6. On the screen, a read cursor 8 of broken line which is composed of plural jointed straight lines and completely traverses the electrophoretic pattern is displayed.

The read cursor can be prepared in an arbitrary part of the electrophoretic pattern, and may be prepared in the upper part of the pattern near the electrophoresis-starting position, or in the lower part of the pattern far away therefrom (having a long migration distance). The input of the positions is generally conducted every lane, that is, the number of the positions to be inputted equals to the number of the lanes. The number of the inputted positions may be larger or smaller than that of the lanes. At least one position is inputted and the starting point and the end point have only to be recognized. The read cursor may be a broken line formed by joining the input positions by straight lines, or the read cursor may be a curved line obtained by subjecting said broken line to operation processing (curvilinear approximation).

Since the prepared cursor coincides with the electrophoretic pattern, analyzers can determine easily and accurately the base sequence of DNA by using the cursor.

In the third place, the read cursor and base name of a band determined using said read cursor are displayed together on the screen.

Figure 7:
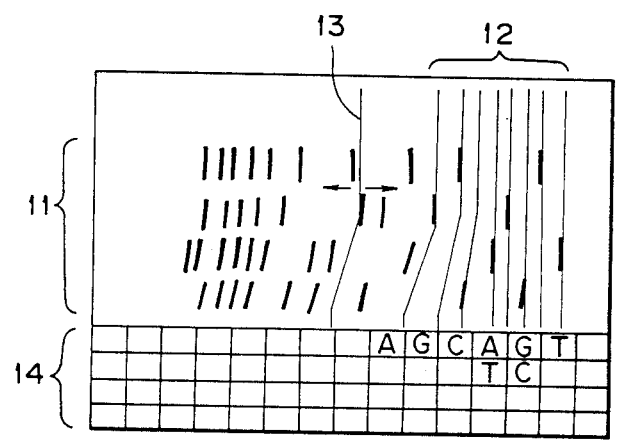
FIGS. 7 to 9 are each a diagram showing an example of an autoradiograph displayed on a screen and illustrates the simultaneous display of read cursors and a base name column.
Figure 8:
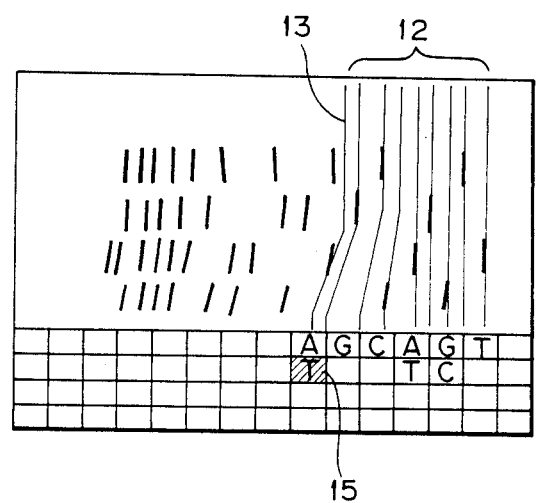
Figure 9:
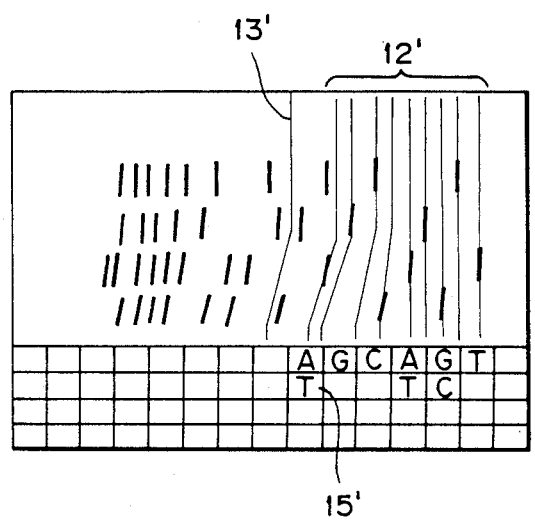

FIGS. 7 to 9 show examples of an autoradiograph of the electrophoretic pattern 11, read cursors 12, 13 (or 12', 13') and a base name column 14, and illustrate the display of the base names together with the read cursors. In FIGS. 7 to 9, the electrophoretic direction is the right and base names (noted by capitals: G, A, T or C) of bands read by using the cursors 12 are displayed in the column 14.

The read cursor 13 (referred to as active cursor) to be used in reading is moved in parallel towards the left or the right and positioned to a band position to be read in next, according to input of said movement of the read cursor. The read cursors 12 (referred to as mark cursor) which have been used in reading may be kept to display on the screen, to make a one-to-one correspondence between bands and base names clear. The active cursor is preferably distinguished from the mark cursor by means of difference of color, solid line and dotted line, difference of brightness, etc., to prevent an error in reading.

The read cursor can be moved by a given space according to a simple input operation by presetting the starting position of movement of the cursor and the distance of the movement. The cursor can be moved at an arbitrary angle in the oblique direction as well as in parallel in the left and right directions. Hence, the cursor can be moved along the pattern even when the lanes are zigzag or the whole pattern is distorted.

Subsequently, base name is displayed in a base name box 15 (blank box) to be entered immediately after the base name corresponding to a lane of the band to which the active cursor positioned is inputted by use of a keyboard, etc. The lanes (1) to (4) include the information on the end bases of (G), (A), (T) and (C), respectively. The base name of band can be determined by utilizing the fact that the two or more bands do not exist at the same position on the different lanes owing to the exclusive combination of the sample.

The blank box 15 to which the base name is entered is preferably distinguished from other boxes of the base name column by means of reverse (see, FIG. 8), on-and-off light, etc., to make the marked point clear and prevent an error in the entering. When the entered base name is not correct, the base name can be changed at once by reentering.

Then, the active cursor is again moved and positioned to the next band position according to input for moving the cursor. At the same time, the marked box 15 changes to be displayed in the same manner as the other boxes where the base names have been determined, and a mark cursor is newly displayed at the position where the active cursor existed. There are displayed mark cursors 12′, an active cursor 13′ and the entered box 15′, as shown in FIG. 9.

In this way, the bands are assigned to base names in order from the lower end of the electrophoretic pattern. After the reading is completed, there are displayed read cursors (mark cursors) in the one-to-one correspondence with the bands and a series of base names entered in the base name column at the lower end of the cursors on the screen. The collation of the base names with the bands and the verification thereof can be easily conducted after the reading or during the reading. When the read cursor does not coincide with the pattern in the course of the assignment of bands, a read cursor in the desired form can be easily prepared and displayed by repeating the aforementioned procedure. The base sequence of DNA is obtained by joining the series of the base names in order from the end. For instance, the following base sequence of DNA is obtained.

T—G—C—A—T—C—G—...

The obtained information on the base sequence of DNA can be stored via the signal processing circuit in a storage means such as a magnetic disk or a magnetic tape, displayed on a screen such as CRT, or recorded on a recording material such as a photosensitive material or a heat-sensitive material.

In the second method of the present invention, the information on the autoradiograph and the base sequence of DNA displayed on the screen as described above are recorded and stored, being separated into three kinds of information, that is, pattern information, cursor information and base sequence information.

First, only information on the autoradiograph of the electrophoretic pattern displayed as an image on the screen is recorded and stored as pattern information. The autoradiograph is recorded and stored in the form of digital image data corresponding to a shading image of FIG. 1, a bird's-eye view of FIG. 2 or a binary image. The digital image data consist of two-dimensional coordinates (x,y) and signal levels (z) corresponding to the pixels.

Figure 10:
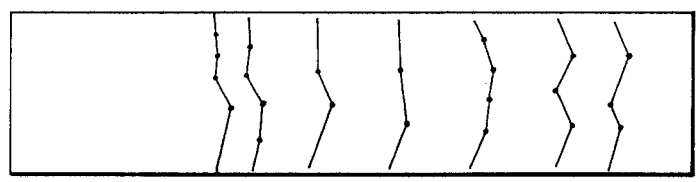
FIG. 10 is a diagram showing an example of plural read cursors in the form of a broken line stored as cursor information.

Secondly, only information on a lot of read cursors fixed onto the electrophoretic pattern (bands) on the screen is independently recorded and stored as cursor information. The cursor information consists of data on the cursors whose number corresponds to the number of the assigned bands, wherein each cursor is numbered according to the sequence of the bands, and two-dimensional coordinates of the nodes of each broken line are also recorded and stored as the data when the cursors are in the form of a broken line. For instance, data on a lot of the read cursors shown in FIG. 10 are stored.

Thirdly, only information on the base names of the assigned bands is independently recorded and stored as base sequence information. In the base sequence information, numbering is made according to the sequence of the bands. For instance, character string data shown in FIG. 8 are stored.

The pattern information and the cursor information are stored, establishing a correspondence therebetween by use of the two-dimensional coordinate fixed to the image (referred to as address correspondence). The cursor information and the base sequence information are stored, establishing a correspondence therebetween by use of the numbers in order of the sequence of the bands on the electrophoretic pattern (referred to as order correspondence).

These three kinds of the information are recorded and stored in a storage means such as a secondary storage and three information files are formed. These information files can be recombined at any time and reproduced on a display means such as CRT, recording materials such as a photosensitive material and a heat-sensitive material. That is, for instance, the three information files in which the pattern information of FIG. 1, the cursor information of FIG. 10 and the base sequence information of FIG. 11 are respectively stored are combined to reproduce a diagram such as FIG. 9.

The storage means (or recording medium) in which the information is stored is not restricted to the secondary storage, and other storage means and recording mediums can be employed provided that three kinds of the information are independently stored keeping the one-to-one correspondence and at any time recombined to reproduce a diagram therefrom. It is not necessary to record and store all the information in the same means or medium. Further, the recording and the storage of the information can be always conducted not only after the analysis but also on the way of the analysis. In the case of using a write/read enable medium such as a magnetic disk, the information can be repeatedly recorded on the once recorded medium.

The analyzed autoradiograph can be easily checked and verified between the assigned bands and the base names thereof by other people in future. When the analysis of the autoradiograph is interrupted, the assignment of bands can be continued from the interrupted point.

Thus determined sequence of the bands (that is, the base sequence of DNA) are verified and further corrected according to the following method (the third and fourth methods) of the present invention.

In the first place, the above-described pattern information on the autoradiograph of the electrophoretic pattern composed of the four electrophoretic rows (lanes), cursor information on the read cursors used in the reading and base sequence information on base names of the assigned bands and the sequence thereof are fed to an apparatus comprising a signal processing circuit, a display means (e.g. CRT) capable of displaying together an autoradiograph, a cursor and base name, and an input means capable of inputting for the verification of the band sequence and further for the correction thereof. The autoradiograph to be analyzed is displayed as an image such as a shading image, a binary image or a bird's-eye view on the display screen on the basis of the pattern information. It is preferred that the apparatus is provided with further an input means capable of inputting for the preparation of cursor and displaying base name and a storage means for the recording and the storage of pattern information, cursor information and base sequence information.

The digital signals corresponding to the autoradiograph stored as pattern information may be previously subjected to the aforementioned signal processing (image processing).

Subsequently, a read cursor is displayed on the screen according to the input for the verification of band's sequence by fixing the cursor to the electrophoretic pattern on the screen so as to allow the cursor to traverse the lanes and to pass through one band, and at the same time, the base name of said band determined is displayed on the screen. The optimum cursor for each band can be immediately displayed based on the cursor information.

The input for the verification of the band's sequence is conducted by a simple keyboard operation such as pushing a verification key. For instance, according to the first key input, a read cursor passing through the position of the lowermost band, which has been stored as information, is displayed and fixed to the pattern. The base name (T) of said band which has been determined is together (simultaneously) displayed on the lower side of the cursor.

According to the next input for the verification of band's sequence (e.g. key input), a read cursor passing through the position of the second band from the lowermost band and the base name of said band are displayed. Thus, it can be verified whether the sequence of the bands is correct or not, while displaying one by one the cursors and the base name of the bands whose sequence has been previously determined. The verification can be made by utilizing the fact that there do not exist two or more bands at the same position on different lanes owing to the exclusive combination of the sample.

On the display screen on the way of the verification, a diagram consisting of the autoradiograph of the electrophoretic pattern, the plural read cursors and the base name column, which is similar to FIG. 9, are displayed. The read cursors may be distinguished between the unused one and the used ones in verifying and the base name column may be also displayed, distinguishing the base name box not verified from the verified boxes, whereby the reversal of the band's sequence and the overlapping or the overlooking of the bands in reading are easily found out. The distinction is made in the same manner as described above. The cursor and the base name box which are not verified are automatically judged as verified ones by the next key input and immediately displayed as a verified cursor and a base name box. At the same time, a cursor identified as the unused one is newly displayed on the screen.

When errors in the band's sequence such as the reversal of the sequence and the overlapping or overlooking of the bands in reading are found in the course of the verification, the sequence of the bands can be corrected according to input on the basis of display screen prior to the next key input.

The correction of the band's sequence is made by deleting the cursor and the base name corresponding to a band read twice from the display screen according to input such as key input, when the overlapping of the band in reading is caused. When the overlooking of a band in reading is caused, the correction is made by additionally displaying a new cursor and new base name corresponding to said band on the screen. When the reversal of the sequence is caused, the correction is made by changing (that is, deleting and adding) the cursor and the base name corresponding to said band on the screen.

In this way, the verification and the correction of the band's sequence are performed, while displaying one by one the cursors and the base names of the sequence-determined bands in order and optionally deleting, adding or changing them.

After the operations for the verification and the optional correction of the band's sequence are completed, the electrophoretic pattern, the read cursors and the base names, the latter two corresponding to the bands one by one, are left on the screen. A series of the bases are jointed sequentially from the end, whereby the base sequence of DNA can be obtained. For instance, the following base sequence of DNA is obtained.

T—G—C—A—T—C—G—...

Alternatively, the sequence of the bands appearing on the autoradiograph can be determined by subjecting the digital signals to signal processing. The automatic analysis by the signal processing is basically conducted in such a manner that positions where signal level is maximum are detected to determine band positions; the bands are sequenced on the base of said positions; and base names are given to the bands based on the lanes to which the bands belongs since the terminal base is restricted by the lanes. This automatic analyzing method is described in more detail in our co-pending U.S. patent applications Ser. No. 849,187, continued as Ser. No. 07/541,197, Ser. No. 854,381, Now U.S. Pat. No. 4,720,786, Ser. No. 897,999, now U.S. Pat. No. 4,802,101, Ser. No. 917,606 and Ser. No. 917,609.

In this case, the obtained band's sequence and the autoradiograph are recorded and stored in an appropriate recording medium as band information and pattern information, respectively. The band information is band data comprising band positions (x,y) represented by a coordinate system fixed to the autoradiograph (that is, a coordinate system which digital signals have) and base names (for instance, G, A, T or C for DNA) to which bands are assigned, as shown in FIG. 12.

The above-mentioned third and fourth methods of the invention can be applied to the results of the automatic analysis of the autoradiograph stored as the pattern information and the band information. For instance, the information $(x_1, y_1, T)$ on the lowermost band of the electrophoretic pattern is extracted from the determined band information as shown in FIG. 12 according to the first key input, and a read cursor which has been previously entered or prepared on the screen is displayed by fixing it to the pattern so as to allow the cursor to pass through the band position $(x_1, y_1)$. The band information may be displayed together on the screen or by switching the screen. In such a case, it is preferred that the extracted band can be recognized immediately by means of a pointer such as an arrow.

The read cursor may be displayed as a straight line which traverses the lanes, and is preferably displayed as a broken line or a curved line along a band of each lane. The read cursor can be prepared in the same manner as afore-described. It is desirable that when the read cursor is fixed to the pattern, the coordinate of the band position which is included in the band information is converted into cursor information (as a set of the coordinates of the nodes of a broken line, in the case of the cursor of broken line). When the read cursor no longer coincides with the electrophoretic pattern in the course of the verification, a cursor in the desired form can be simply prepared and displayed by repeating a similar procedure to that afore-described.

Subsequently, the second band from the lowermost band is extracted from the band information, when the input for the verification of the band's sequence is done. For instance, said band is indicated by a pointer on the screen displaying the band information. A read cursor passing through the band position and the base name of said band are displayed on the screen displaying the electrophoretic pattern. Thus, while displaying the cursor and the base names of the bands whose sequence has been previously determined, it is verified whether the band's sequence is correct or not. Further, the correction of the band's sequence is made in the same manner as described above, and after the verification and the correction, the electrophoretic pattern, the read cursors and the base names in the one-to-one correspondence with each other are left on the screen.

It is desirable that the information on the electrophoretic pattern, the read cursors and the base sequence is recorded and stored as pattern information, cursor information and base sequence information separately, being kept the corresponding relationships therebetween, in the same manner as afore-described.

In the latter case that the analytic results of the autoradiograph comprises the pattern information (e.g. digital image data corresponding to pixels) and the band information when determining the band's sequence, said analysis information is changed to comprise the pattern information (digital image data corresponding to the display image), the cursor information and the base sequence information after the verification and correction.

In the above-mentioned example, there has been described the case where the exclusive combination of the mixture (G, A, T, C) of base-specific DNA fragments as a sample is used, but the analyzing method of the present invention is by no means limited to said combination, and other combinations can be used. For instance, a combination of (G, G+A, A+C, C) may be used. Further, the method of the present invention can also be applied to the mixture (for instance, a combination of G, A, U, C) of base-specific RNA fragments.

I claim:

1. A method of analyzing an autoradiograph of plural resolved rows which are formed by resolving base-specific DNA fragments or base-specific RNA fragments labeled with a radioactive element in one-dimensional direction on a support medium, to determine the base sequence of nucleic acids, which comprises steps of:

(1) obtaining digital signals corresponding to the autoradiograph by placing the support medium and a stimulable phosphor sheet comprising a stimulable phosphor together in layers to record the autoradiograph of plural resolved rows on the phosphor sheet as an energy-stored image, irradiating said phosphor sheet with stimulating rays and photoelectrically detecting the autoradiograph as stimulated emission; and electrically displaying the autoradiograph as an image on a screen on the basis of digital signals corresponding to said autoradiograph;

(2) preparing and displaying a read cursor on the screen; and (3) determining the name of a base to which a band is assigned by using the read cursor and displaying the name of said base on the screen together with the read cursor.

2. The method of analyzing an autoradiograph as claimed in claim 1, wherein said read cursor is displayed in the form of a broken line or a curved line as to allow the cursor to traverse the resolved rows along a band of each row in the second step.

3. The method of analyzing an autoradiograph as claimed in claim 2, wherein said read cursor is prepared by drawing straight lines or an arc which passes through at least one given position according to input of said position in the second step.

4. The method of analyzing an autoradiograph as claimed in claim 3, wherein said position is inputted by using a pointing device.

5. The method of analyzing an autoradiograph as claimed in claim 4, wherein said pointing device is a mouse cursor.

6. The method of analyzing an autoradiograph as claimed in claim 1, wherein said base name is displayed in the form of a character and/or a symbol at the end of the read cursor in the third step.

7. The method of analyzing an autoradiograph as claimed in claim 1, wherein said autoradiograph is displayed as a shading image, a binary image or an image represented by multi-displaying two-dimensional waveforms composed of position along the resolving direction and image density at regular intervals in a direction perpendicular to the resolved direction in the first step.

8. The method of analyzing an autoradiograph as claimed in claim 1, wherein a read cursor to be used in reading a band subsequent to any read cursor having assigned a band to a base displayed in the third step, is distinguishable in appearance from such prior read cursor.

9. The method of analyzing an autoradiograph as claimed in claim 1, wherein a name of base to which a band is assigned displayed subsequent to any name of base to which a band has been assigned displayed in the third step, is distinguishable in appearance from such prior name of base.

10. A method of analyzing an autoradiograph of plural resolved rows which are formed by resolving base-specific DNA fragments or base-specific RNA fragments labeled with a radioactive element in a one-dimensional direction on a support medium, to determine the base sequence of nucleic acids, which comprises the steps of:

(1) obtaining digital signals corresponding to an autoradiograph and electrically displaying the autoradiograph as an image on a screen on the basis of said digital signals;

wherein said digital signals are obtained by placing the support medium and a radiosensitive material together in layers to record the autoradiograph of plural resolved rows on the radiosensitive material as a visible image and photoelectrically reading out the autoradiograph visualized on said radiosensitive material;

(2) preparing and displaying a read cursor on the screen; and (3) determining the name of a base to which a band is assigned by using the read cursor and displaying the name of said base on the screen together with said read cursor.

11. A method of analyzing an autoradiograph of a resolved pattern comprising plural resolved rows which are formed by resolving base-specific DNA fragments or base-specific RNA fragments labeled with a radioactive element in a one-dimensional direction on a support medium, to determine the base sequence of nucleic acids, which comprises separating information on said autoradiograph and the base sequence of nucleic acid determined on the basis of the autoradiograph into the following three kinds of information:

(1) information on the autoradiograph of the resolved pattern;

(2) information on plural read cursors which pass through bands on the autoradiograph and indicate relative positions on the bands; and (3) information on the sequence of bases to which the bands on the autoradiograph are assigned;

establishing a correspondence between the pattern information (1) and the cursor information (2) and a correspondence between the cursor information (2) and the base sequence information (3), wherein said information is in the form of digital signals corresponding to the autoradiograph obtained by placing the support medium and a stimulable phosphor sheet comprising a stimulable phosphor together in layers to record the autoradiograph of plural resolved rows on the phosphor sheet as an energy-stored image, irradiating said phosphor sheet with stimulating rays and photoelectrically detecting the autoradiograph as stimulated emission; and recording and storing said information.

12. The method of analyzing an autoradiograph as claimed in claim 11, wherein said correspondence between the pattern information and the cursor information is established by coordinates, and said correspondence between the cursor information and the base sequence information is established by order.

13. The method of analyzing an autoradiograph as claimed in claim 11, wherein said pattern information, cursor information and base sequence information are stored in a secondary storage.

14. The method of analyzing an autoradiograph as claimed in claim 11, wherein said pattern information, cursor information and base sequence information are recorded on the same recording medium.

15. The method of analyzing an autoradiograph as claimed in claim 11, wherein said pattern information includes a shading image, a binary image or an image represented by multi-displaying two-dimensional waveforms composed of position along the resolving direction and image density at regular intervals in a direction perpendicular to the resolved direction.

16. The method of analyzing an autoradiograph as claimed in claim 11, wherein said cursor information includes a plurality of broken lines or curved lines which traverse the resolved rows along a band of each row.

17. The method of analyzing an autoradiograph as claimed in claim 11, wherein said base sequence information includes a series of characters and/or symbols.

18. A method of analyzing an autoradiograph of a resolved pattern comprising plural resolved rows which are formed by resolving base-specific DNA fragments or base-specific RNA fragments labeled with a radioactive element in a one-dimensional direction on a support medium, to determine the base sequence of nucleic acids, which comprises separating information on said autoradiograph and the base sequence of nucleic acid determined on the basis of the autoradiograph into the following three kinds of information:

(1) information on the autoradiograph of the resolved pattern;

(2) information on plural read cursors which pass through bands on the autoradiograph and indicate relative positions on the bands; and (3) information on the sequence of bases to which the bands on the autoradiograph are assigned;

establishing a correspondence between the pattern information (1) and the cursor information (2) and a correspondence between the cursor information (2) and the base sequence information (3), wherein digital signals corresponding to the autoradiograph are obtained by placing the support medium and a radiosensitive material together in layers to record the autoradiograph of plural resolved rows on the radiosensitive material as a visible image and photoelectrically reading out the autoradiograph visualized on said radiosensitive material; and recording and storing said information.

19. A method of analyzing an autoradiograph of a resolved pattern comprising plural resolved rows which are formed by resolving base-specific DNA fragments or base-specific RNA fragments labeled with a radioactive element in a one-dimensional direction on a support medium, to determine the base sequence of nucleic acids, which comprises the steps of:

(1) determining a sequence of bands by subjecting digital signals corresponding to the autoradiograph to signal processing and electrically displaying an autoradiograph in which sequence of bands has been determined as an image on a screen on the basis of digital signals corresponding to said autoradiograph;

(2) preparing and displaying a read cursor on the screen to fix the cursor to the autoradiograph so as to allow the cursor to traverse the resolved rows and to pass through one band position according to input for verification of the band's sequence;

(3) verifying the sequence of the band and displaying the base name of said band together on the screen;

(4) preparing and displaying another read cursor on the screen to fix the cursor to the autoradiograph so as to allow the cursor to pass through a band position adjacent to the band to which the cursor is fixed in step (2) according to input for verification of the band's sequence;

(5) verifying the sequence of the band and displaying the base name of said band together on the screen; and (6) repeating step (4) to verify the determined sequence of the bands on the autoradiograph.

20. The method of analyzing an autoradiograph as claimed in claim 19, wherein said band to which the cursor is fixed in step 2 is the lowermost band and the sequence of the bands is verified in order from the lowermost band in steps (2) through (5).

21. The method of analyzing an autoradiograph as claimed in claim 19, wherein said input for verification of the band's sequence in steps (2) through (5) is based on the determined sequence of the bands.

22. The method of analyzing an autoradiograph as claimed in claim 19, wherein said read cursor is displayed in the form of a broken line or a curved line in steps (2) through (5).

23. The method of analyzing an autoradiograph as claimed in claim 19, wherein said autoradiograph of the resolved pattern displayed as an image, said plural read cursors fixed to the autoradiograph and the verified sequence of the bands are separated as pattern information (1), cursor information (2) and base sequence information (3) from one another, and said information is recorded and stored in such a manner as to establish a correspondence between (1) and (2) and a correspondence between (2) and (3).

24. The method of analyzing an autoradiograph as claimed in claim 19, wherein said autoradiograph is displayed as a shading image, a binary image or an image represented by multi-displaying two-dimensional waveforms composed of position along the resolving direction and image density at regular intervals in a direction perpendicular to the resolved direction in step (1).

25. A method of analyzing an autoradiograph of a resolved pattern comprising plural resolved rows which are formed by resolving base-specific DNA fragments or base-specific RNA fragments labeled with a radioactive element in one-dimensional direction on a support medium, to determine the base sequence of nucleic acids, which comprises steps of:
(1) obtaining digital signals corresponding to an autoradiograph and electrically displaying the autoradiograph in which sequence of bands has been determined as an image on a screen on the basis of digital signals corresponding to said autoradiograph, wherein said digital signals are obtained by placing the support medium and a stimulable phosphor sheet comprising a stimulable phosphor together in layers to record the autoradiograph of plural resolved rows on the phosphor sheet as an energy-stored image, irradiating said phosphor sheet with stimulating rays and photoelectrically detecting the autoradiograph as stimulated emission;
(2) preparing and displaying a read cursor on the screen to fix the cursor to the autoradiograph so as to allow the cursor to traverse the resolved rows and to pass through one band position according to input for verification of the band's sequence;
(3) verifying the band's sequence and displaying the base name of said band together on the screen;
(4) preparing and displaying a read cursor on the screen to fix the cursor to the autoradiograph so as to allow the cursor to pass through a band position adjacent to the band to which the cursor is fixed in the second step according to input for verification of the band's sequence, (5) verifying the band's sequence and displaying the base name of said band together on the screen; and
(6) repeating step (4) and (5) to verify the determined sequence of the bands on the autoradiograph.

26. A method of analyzing an autoradiograph of a resolved pattern comprising plural resolved rows which are formed by resolving base-specific DNA fragments or base-specific RNA fragments labeled with a radioactive element in one-dimensional direction on a support medium, to determine the base sequence of nucleic acids, which comprises steps of:
(1) obtaining digital signals corresponding to an autoradiograph and electrically displaying the autoradiograph in which sequence of bands has been determined as an image on a screen on the basis of digital signals corresponding to said autoradiograph; wherein said digital signals are obtained by placing the support medium and a radiosensitive material together in layers to record the autoradiograph of plural resolved rows on the radiosensitive material as a visible image and photoelectrically reading out the autoradiograph visualized on said radiosensitive material;
(2) preparing and displaying a read cursor on the screen to fix the cursor to the autoradiograph so as to allow the cursor to traverse the resolved rows and to pass through one band position according to input for verification of the band's sequence;
(3) verifying the band's sequence and displaying the base name of said band together on the screen;
(4) preparing and displaying a read cursor on the screen to fix the cursor to the autoradiograph so as to allow the cursor to pass through a band position adjacent to the band to which the cursor is fixed in the second step according to input for verification of the band's sequence and displaying the base name of said band together on the screen; and
(6) repeating step (4) and (5) to verify the determined sequence of the bands on the autoradiograph.

27. A method of analyzing an autoradiograph of a resolved pattern comprising plural resolved rows which are formed by resolving base-specific DNA fragments or base-specific RNA fragments labeled with a radioactive element in one-dimensional direction on a support medium, to determine the base sequence of nucleic acids, which comprises the steps of:
(1) determining the sequence of bands by subjecting digital signals corresponding to an autoradiograph to signal processing and electrically displaying the autoradiograph in which the sequence of bands has been determined as an image on a screen on the basis of digital signals corresponding to said autoradiograph;
(2) preparing and displaying a read cursor on the screen to fix the cursor to the autoradiograph so as to allow the cursor to traverse the resolved rows and to pass through one band position according to input for verification of the band's sequence;
(3) verifying the band's sequence and displaying the base name of said band together on the screen;
(4) preparing and displaying a second read cursor on the screen to fix the cursor to the autoradiograph so as to allow the cursor to pass through a band position adjacent to the band to which the cursor is fixed in the second step according to input for verification of the band's sequence (5) verifying the band's sequence and displaying the base name of said band together on the screen;

(6) deleting, adding or changing the read cursor and/or the base name displayed in step (4) according to input, when there is inputted information on the basis of the display screen;

(7) verifying the determined sequence of the bands by repeating in order steps (4), (5) and (6); and (8) correcting the determined sequence of the bands as required.

28. The method of analyzing an autoradiograph as claimed in claim 27, wherein said band to which the cursor is fixed in step (2) is the lowermost band and the sequence of the bands is verified and corrected in order from the lowermost band in steps (2) through (8).

29. The method of analyzing an autoradiograph as claimed in claim 27, wherein said input for verification of the band's sequence in steps (2), (3) and (4) is based on the determined sequence of the bands.

30. The method of analyzing an autoradiograph as claimed in claim 27, wherein said read cursor is displayed in the form of a broken line or a curved line in steps (2), (3) and (4).

31. The method of analyzing an autoradiograph as claimed in claim 27, wherein said autoradiograph of the resolved pattern displayed as an image, said plural read cursors fixed to the autoradiograph, and the verified and corrected sequence of the bands are separated as pattern information (1), cursor information (2) and base sequence information (3) from one another, and said information is recorded and stored in such a manner as to establish a correspondence between (1) and (2) and a correspondence between (2) and (3).

32. The method of analyzing an autoradiograph as claimed in claim 27, wherein said autoradiograph is displayed as a shading image, a binary image or an image represented by multi-displaying two-dimensional waveforms composed of position along the resolving direction and image density at regular intervals in a direction perpendicular to the resolved direction in step (1).

33. A method of analyzing an autoradiograph of a resolved pattern comprising plural resolved rows which are formed by resolving base-specific DNA fragments or base-specific RNA fragments labeled with a radioactive element in a one-dimensional direction on a support medium, to determine the base sequence of nucleic acids, which comprises the steps of:
(1) obtaining digital signals and electrically displaying an autoradiograph in which a sequence of bands has been determined as an image on a screen on the basis of said digital signals corresponding to said autoradiograph, wherein said digital signals are obtained by placing the support medium and a stimulable phosphor sheet comprising a stimulable phosphor together in layers to record the autoradiograph of plural resolved rows on the phosphor sheet as an energy-stored image, irradiating said phosphor sheet with stimulating rays and photoelectrically detecting the autoradiograph as stimulated emission;

(2) preparing and displaying a read cursor on the screen to fix the cursor to the autoradiograph so as to allow the cursor to traverse the resolved rows and to pass through one band position according to input for verification of the band's sequence, and displaying the base name of said band together on the screen;

(3) preparing and displaying a second read cursor on the screen to fix the cursor to the autoradiograph so as to allow the cursor to pass through a band position adjacent to the band to which the cursor is fixed in step (2) according to input for verification of the band's sequence, (4) verifying the band's sequence and displaying the base name of said band on the screen;

(5) deleting, adding or changing the read cursor and/or the base name displayed in step (4) according to input, when there is inputted information on the basis of the display screen;

(6) verifying the determined sequence of the bands by repeating in order steps (3), (4) and (5); and (7) correcting the determined sequence of the bands as required.

34. A method of analyzing an autoradiograph of a resolved pattern comprising plural resolved rows which are formed by resolving base-specific DNA fragments or base-specific RNA fragments labeled with a radioactive element in a one-dimensional direction on a support medium, to determine the base sequence of nucleic acids, which comprises the steps of:
(1) obtaining digital signals and electrically displaying an autoradiograph in which sequence of bands has been determined as an image on a screen on the basis of said digital signals corresponding to said autoradiograph, wherein said digital signals are obtained by placing the support medium and a radiosensitive material together in layers to record the autoradiograph of plural resolved rows on the radiosensitive material as a visible image and photoelectrically reading out the autoradiograph visualized on said radiosensitive material;

(2) preparing and displaying a read cursor on the screen to fix the cursor to the autoradiograph so as to allow the cursor to traverse the resolved rows and to pass through one band position according to input for verification of the band's sequence, and displaying the base name of said band on the screen;

(3) preparing and displaying a second read cursor on the screen to fix the cursor to the autoradiograph so as to allow the cursor to pass through a band position adjacent to the band to which the cursor is fixed in step (2) according to input for verification of the band's sequence, (4) verifying the band's sequence and displaying the base name of said band on the screen;

(5) deleting, adding or changing the read cursor and/or the base name displayed in the step (4) according to input, when there is inputted information on the basis of the display screen;

(6) verifying the determined sequence of the bands by repeating in order steps (3), (4) and (5); and (7) correcting the determined sequence of bands as required.

35. A method of analyzing an autoradiograph of plural resolved rows which are formed by resolving base-specific DNA fragments or base-specific RNA fragments labeled with a radioactive element in one-dimensional direction on a support medium to determine the base sequence of the nucleic acids in said fragments which comprises the steps of:

(1) obtaining digital signals corresponding to the autoradiograph and processing said digital signals to electrically display the autoradiograph as an image on a screen;

(2) preparing a read cursor by drawing straight lines or an arc which passes through at least one given position on said image and displaying said read cursor on said screen so that said read cursor is capable of traversing the resolved rows along a band of each row; and (3) assigning to a band the name of a base, determining the name of said base with said read cursor, and displaying the same of said base and said read cursor on the screen.

* * * * *